United States Patent
Grosshauser et al.

(10) Patent No.: US 9,822,404 B2
(45) Date of Patent: Nov. 21, 2017

(54) CONTROL FOR DIAGNOSTIC ASSAY

(71) Applicant: QIAGEN GMBH, Hildend (DE)

(72) Inventors: Gerd Grosshauser, Hildn (DE); Andy Wende, Hilden (DE); Ralf Himmelreich, Langenfeld (DE)

(73) Assignee: Qiagen GmbH, Hilden (DE)

( * ) Notice: Subject to any disclaimer, the term of this patent is extended or adjusted under 35 U.S.C. 154(b) by 264 days.

(21) Appl. No.: 14/441,112

(22) PCT Filed: Nov. 7, 2013

(86) PCT No.: PCT/EP2013/073205
§ 371 (c)(1),
(2) Date: May 6, 2015

(87) PCT Pub. No.: WO2014/072367
PCT Pub. Date: May 15, 2014

(65) Prior Publication Data
US 2015/0292000 A1    Oct. 15, 2015

(30) Foreign Application Priority Data
Nov. 7, 2012  (EP) .................................... 12007553

(51) Int. Cl.
*C12Q 1/68* (2006.01)
(52) U.S. Cl.
CPC .......... *C12Q 1/686* (2013.01); *C12Q 1/6806* (2013.01); *C12Q 1/6848* (2013.01)
(58) Field of Classification Search
None
See application file for complete search history.

(56) References Cited

U.S. PATENT DOCUMENTS

| | | | | |
|---|---|---|---|---|
| 2004/0259162 A1* | 12/2004 | Kappel | .................... | C07K 1/36 435/7.1 |
| 2006/0046261 A1* | 3/2006 | Porter | .................... | C07K 1/36 435/6.12 |
| 2007/0105094 A1* | 5/2007 | Fujita | ............... | G01N 33/54326 435/5 |
| 2008/0003575 A1* | 1/2008 | Michalik | ............ | C12N 15/1003 435/6.12 |
| 2009/0018323 A1* | 1/2009 | Erbacher | .................... | C08F 8/30 536/25.41 |
| 2010/0099150 A1* | 4/2010 | Fang | .................... | C07K 14/765 435/91.5 |
| 2011/0059547 A1* | 3/2011 | Dehal | ............... | B01L 3/502715 436/174 |
| 2011/0165676 A1* | 7/2011 | Hopkins | .................. | C12N 1/08 435/378 |

FOREIGN PATENT DOCUMENTS

| | | |
|---|---|---|
| EP | 0726312 A2 | 8/1996 |
| EP | 0770689 A2 | 5/1997 |
| EP | 1319716 A1 | 6/2003 |
| WO | 2008/077017 A2 | 6/2008 |
| WO | 2008/152102 A1 | 12/2008 |

OTHER PUBLICATIONS

Zhian Zhang et al; "Direct DNA Amplification from Crude Clinical Samples Using a PCR Enhancer Cocktail and Novel Mutants of Taq"; The Journal of Molecular diagnostics; vol. 12, No. 2; Mar. 1, 2010; pp. 152-161; XP-055001258.

Johan De Vries; "PCR on Cell Lysates Obtained from Whole Blood Circumvents DNA Isolation"; Clinical Chemistry; vol. 47, No. 9; Jan. 1, 2001; pp. 1701-1702; XP055050934.

* cited by examiner

*Primary Examiner* — Aaron Priest
(74) *Attorney, Agent, or Firm* — Rankin, Hill & Clark LLP

(57) ABSTRACT

A method for determining whether a lysate contains sufficient biological sample material for a nucleic acid amplification reaction that includes preparing the lysate in the presence of at least one compound that inhibits the amplification reaction if insufficient biological sample material was present during preparation of the lysate, but does not inhibit the amplification reaction if sufficient biological sample material was present during preparation of the lysate, subjecting the lysate to the amplification reaction, and analyzing a result of the amplification reaction. Due to the presence of the compound in the amplification reaction, no amplification signal is obtained if insufficient biological sample material was present during preparation of the lysate but an amplification signal is obtained if sufficient biological sample material was present during preparation of the lysate. The invention allows for reliable identification of false negatives that occur because insufficient sample material was subjected to the amplification assay.

10 Claims, 2 Drawing Sheets

CONTROL FOR DIAGNOSTIC ASSAY

FIELD OF THE INVENTION

The present invention pertains to a method for controlling the correct performance of an amplification reaction. Said method allows to control that a biological sample was subjected to a diagnostic test thereby allowing to identify false negative assay results. The method is of particular use in the field of clinical diagnostics.

BACKGROUND

Many diagnostic tests used in the current art involve the amplification of a target nucleic acid. Respective amplification based assays are in particular used in order to detect the presence or absence of a target nucleic acid, such as for example a pathogen nucleic acid, in a biological sample material. If the target nucleic acid is comprised in the sample, a signal is obtained in the amplification reaction thereby indicating that the target nucleic acid is present and that, for example, a patient is infected with a certain pathogen. There is a high demand to control that the assay was performed accurately and accordingly, and thus provides a reliable result.

A major problem in particular in the field of clinical diagnostics is the occurrence of false negative results. False negatives may occur for several reasons. E.g. false negatives may occur due to a failure of one or more reagents that are used in the amplification reaction, due to a failure of thermal cycling or by an inhibition of the amplification reaction. However, false negatives are also attributable to that no or not enough sample material was subjected to the assay. The transfer of sample material is a critical step, in particular in high-throughput applications and when performing the respective tests using automated platforms. E.g. the biological sample such as a swab sample is transferred into the lysis composition by wiping off, shaking or similar means. Such transfers are prone to errors because no or not enough sample material may be transferred in order to allow a valid interpretation of the test results. Similar problems can also occur when handling liquid biological samples, e.g. when pipetting errors occur. The occurrence of false negatives is a major problem in the field of clinical diagnostics, e.g. because necessary treatments cannot be initiated in due time or subjects infected with a certain pathogen are not properly identified. E.g. in hospitals incoming patients are often routinely screened for the presence of certain pathogens such as MRSA and in case of a positive result are put into quarantine. A false negative in such a setting would allow the spread of the disease/pathogen.

In order to identify false negative assay results that are due to failure of the amplification reaction, it is common in the prior art to include an internal control in each amplification reaction. Thus, for each analysed biological sample, a respective internal control is usually included in the amplification reaction. As internal control, nucleic acids such as DNA or RNA (in case of a reverse transcription amplification) are commonly used. A respective internal control nucleic acid is either added separately to the amplification reaction or it can be directly included in the reagents that are used for performing the amplification. For example, a respective internal control can be comprised in the amplification master mix. Primers and/or probes for detecting the respective internal control are also added. Likewise, they can be added separately to the amplification reaction or may be comprised in the amplification master mix. If the amplification reaction works properly, an amplification signal is obtained, thereby indicating that the amplification reaction is valid. Thereby, false negatives that are due to a failure of the amplification reaction can be properly identified because if the amplification reaction did not work accurately, no amplification signal is obtained for the internal control.

However, a respective internal control cannot identify false negatives that occur because either no or not enough sample material was subjected to the assay, because also in this case an amplification signal will be obtained for the internal control because the control is added separately from the biological sample to the amplification reaction. However, the lack of sufficient sample material in the amplification assay can be an important error source that leads to false negative results. In particular, automated protocols that are performed using robotic systems are susceptible to such errors, for example because the sample transfer, e.g. the pipetting, did not work accurately what may result in that either no or not enough sample material was subjected to the assay in order to provide a reliable result. Such problems also occur if the samples are processed manually, in particular in high-throughput applications. Furthermore, for many sample types such as for example swab samples, the transfer of the sample material is particularly difficult. If no sufficient sample material is subjected to the lysis reaction and thus to the amplification reaction, this leads to false negative results in the assay.

Therefore, there is a high demand for methods that allow to identify false negatives and thus invalid assays that are due to that no sufficient sample material was subjected to the amplification based analytical assay.

It is the object to overcome at least one drawback of the prior art methods. In particular, it is the object of the present invention to provide a simple method for controlling that a biological sample material was included in an amplification-based assay. Furthermore, it is the object of the present invention to provide an improved amplification assay, which allows to identify false negatives that occur because insufficient sample material was subjected to the assay.

SUMMARY OF THE INVENTION

The present inventors found that including a compound in the lysate which inhibits the amplification reaction if no sufficient biological sample material was subjected to the assay, but which does not inhibit the amplification reaction if sufficient biological sample material was subjected to the assay, allows to control that a valid amount of sample material was included in the amplification assay and accordingly allows to determine that the assay result is reliable. In the method according to the present invention, an amplification signal is only obtained if a valid amount of biological sample material was used for preparing the lysate. If no valid amount of sample material was used, no amplification signal is obtained. Thereby, the present invention provides a reliable control method that allows to identify false negatives that may occur if no or an insufficient amount of biological sample material was subjected to the assay. Thereby, a valuable further control is provided that improves the safety of amplification based analytical assays, in particular diagnostic assays.

Therefore, according to a first aspect, a method is provided for controlling that a lysate obtained from sufficient biological sample material was subjected to a nucleic acid amplification reaction, comprising a) using a composition for preparing a lysate, wherein said composition comprises at least one compound (A), wherein compound (A) inhibits the amplification reaction if no sufficient biological sample material was added for obtaining the lysate but does not inhibit the amplification reaction if sufficient biological sample material was added for obtaining the lysate;

b) optionally further processing the lysate;

c) using at least a portion of the lysate in an amplification reaction;

wherein said method comprises analyzing the amplification result, wherein due to the presence of compound (A) in the amplification reaction, no amplification signal is obtained if no sufficient biological sample material was added for obtaining the lysate but wherein an amplification signal is obtained if sufficient biological sample material was added for obtaining the lysate.

The method according to the invention allows to control that a valid amount of sample material was used for preparing the lysate and accordingly was subjected to the amplification assay. In the method according to the present invention, the lysate that is obtained from the biological sample material is directly used in the amplification reaction. Therefore, no nucleic acid purification is performed prior to performing the amplification reaction. That no nucleic acid purification is performed prior to performing the amplification reaction is an advantage because the method is rapid, requires only few preparation steps and furthermore, saves costs for reagents. Thus, the amplification method according to the present invention is particularly suitable for high-throughput applications and furthermore, is particularly suitable for automation and lab-on-a-chip (LoC) approaches. That the lysate that is subjected to the amplification reaction was indeed prepared using sufficient biological sample material is controlled due to the use of compound (A) during lysis. An amplification signal is only obtained if a valid amount of biological sample material was used for obtaining the lysate. If no valid amount of sample material was used, no amplification signal is obtained because in this case compound (A) inhibits the amplification reaction. The amplification result is then analysed in order to identify false negative results. Thereby, the present invention provides a suitable control method that improves the accuracy of the assay by allowing to identify false negative results that may occur because either no or not enough sample material was added for obtaining the lysate.

According to a second aspect, a method is provided for amplifying a nucleic acid comprising subjecting a lysate to an amplification reaction, wherein said amplification reaction comprises at least one compound (A) which comprises at least one anionic group, wherein compound (A) inhibits the amplification reaction if no sufficient biological sample material was added for obtaining the lysate but does not inhibit the amplification reaction if sufficient biological sample material was added for obtaining the lysate and wherein said method comprises analyzing the amplification result, wherein due to the presence of compound (A) in the amplification reaction, no amplification signal is obtained if no sufficient biological sample material was added for obtaining the lysate but wherein an amplification signal is obtained if sufficient biological sample material was added for obtaining the lysate.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
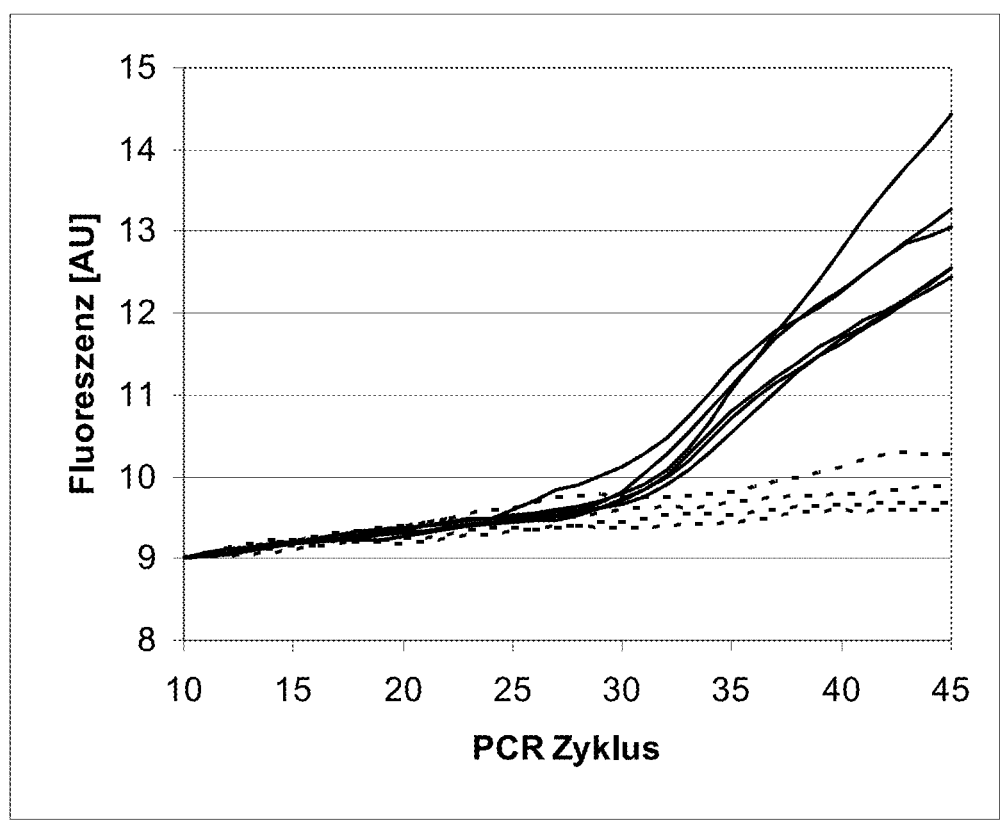
FIG. 1: PCR amplification results using lysates that were obtained by adding a blood sample (solid lines) or that were obtained without the addition of blood (dotted lines) (see example 1).

The present inventions provides a method for controlling that a lysate obtained from sufficient biological sample material was subjected to a nucleic acid amplification reaction, comprising a) using a composition for preparing a lysate, wherein said composition comprises at least one compound (A), which preferably comprises at least one anionic group, wherein compound (A) inhibits the amplification reaction if no sufficient biological sample material was added for obtaining the lysate but does not inhibit the amplification reaction if sufficient biological sample material was added for obtaining the lysate;

b) optionally processing the lysate;

c) using at least a portion of the lysate in an amplification reaction;

wherein said method comprises analyzing the amplification result, wherein due to the presence of compound (A) in the amplification reaction, no amplification signal is obtained if no sufficient biological sample material was added for obtaining the lysate, but wherein an amplification signal is obtained if sufficient biological sample material was added for obtaining the lysate.

The term "no sufficient sample material" and similar expressions used herein in particular refer to scenarios wherein either no sample material was added for obtaining the lysate or wherein not enough sample material was added in order to allow a reliable performance of the amplification reaction.

The individual steps of the method as well as preferred embodiments thereof will now be described in detail.

In step a), a lysate is obtained. The preparation of the lysate involves the use of a composition which comprises at least one compound (A) which preferably comprises at least one anionic group. Compound (A) acts as inhibitor of the amplification reaction if no sufficient biological sample material was added during preparation of the lysate. However, compound (A) does not act as inhibitor of the amplification reaction, if sufficient biological sample material was added to obtain the lysate. Thereby, false negatives that are due to an invalid transfer of sample material (either no or not enough sample material) can be securely identified and can be reported as invalid test result. Also more than one and thus a plurality of compounds (A) can be used during preparation of the lysate.

Preferably, the lysate is prepared by contacting the biological sample with a suitable lysis composition. Said lysis composition, which preferably is a lysis solution, may comprise at least one reagent that promotes the lysis of the biological sample. Preferably, the lysis composition comprises a detergent for said purpose. Suitable embodiments are described subsequently. Preferably, compound (A) is comprised in the lysis composition that is used for lysing the biological sample. Depending on the composition of the lysis solution, lysis may be directly initiated. Preferably, lysis of the biological sample is promoted and hence assisted by a heat incubating step to provide the lysate. Suitable and preferred lysis methods will also be described in the following.

Because at least one compound (A) was used during preparation of the lysate and no nucleic acid purification is performed, compound (A) is also comprised in the obtained lysate. In step b), the obtained lysate is optionally processed, e.g. cleared. At least an aliquot of the obtained lysate, which optionally is cleared in advance, is subjected to the amplification reaction in step c). Thereby, compound (A) is also transferred into the amplification reaction where it acts as inhibitor if no sufficient amount of biological sample was added for lysis.

The concentration of compound (A) in the lysate that is suitable for obtaining the essential effect depends in particular on the compound (A) that is used, the type and amount of processed sample material and furthermore, on the amount of lysate that is subjected to the subsequent amplification reaction. The concentration of compound (A) must be chosen such that when the lysate is subjected to the amplification reaction, compound (A) inhibits the amplification reaction if no sufficient sample material was added for obtaining the lysate while it does not inhibit the amplification reaction if sufficient biological sample material was added for obtaining the lysate. The suitable concentration of compound (A) in the lysate strongly depends on the amount of lysate that is subjected to the amplification reaction. E.g., if only a small aliquot of the obtained lysate is added to an aqueous amplification reaction, the concentration of compound (A) in the amplification reaction is diluted compared to the lysate. In such cases, higher concentrations of compound (A) should be present in the lysate to ensure that even though only a small volume of lysate was subjected to the amplification reaction, compound (A) is present in the amplification reaction in a concentration wherein it can inhibit the amplification reaction if no or not enough sample material was added for obtaining the lysate. Such dilution effects do not occur or occur to a lesser extent if the lysate is e.g. used for reconstituting a dry reagent composition comprising amplification reagents as will be described subsequently. In such cases, the predominant volume of the amplification reaction is attributable to the lysate that is used for reconstitution. Furthermore, the concentration of compound (A) must be sufficiently low to ensure that the amplification reaction is not inhibited when the aliquot of the lysate that was obtained from sufficient sample material is subjected to the amplification reaction. Suitable concentrations for individual settings can be determined for individual embodiments of compound (A), amounts and types of biological sample materials to be processed and lysate volumes to be transferred into the amplification reaction following the teachings described herein using routine experiments.

According to one embodiment, compound (A) does not only not inhibit the amplification reaction if sufficient biological sample material was added for lysis. Preferably, compound (A) improves the amplification reaction by depleting inhibitors that are released during lysis of the biological sample. The term "depletion" of inhibitors and similar terms used herein are used in a broad sense and do not include a limitation regarding the mode of action. In particular, said terms include e.g. unspecific binding, e.g. complexing, of inhibitors by compound (A) and the like. An inhibitor released from the biological sample is depleted in this sense, if the subsequent amplification reaction shows an improved performance due to the addition of compound (A) during lysis compared to when compound (A) is not used during lysis (if sufficient biological sample material was added for lysis). In this preferred embodiment, compound (A) basically inhibits or counteracts the inhibitory action of inhibitors that are released during lysis of the biological sample. By depleting inhibitors that are released from the biological sample during lysis, compound (A) prevents or reduces the inhibition of the amplification reaction, preferably by unspecifically complexing inhibitors that are released during lysis of the biological sample. Thus, preferably, compound (A) serves a dual function. If no or not enough biological sample material was added during preparation of the lysate, compound (A) is present in a concentration in the amplification reaction wherein it inhibits the amplification reaction, thereby allowing to identify false negatives that occur because no or not enough biological sample material was added for lysis. However, if sufficient biological sample material is added for lysis, compound (A) depletes, i.e. "inactivates" amplification inhibitors that are released from the biological sample during lysis, thereby improving the performance of the subsequent amplification reaction. E.g. typical amplification inhibitors which usually originate from the biological sample and are released during lysis include but are not limited to proteoglycans, proteins and sugars. In the method of the present invention, wherein the obtained lysate is without prior purification of the nucleic acids subjected to the amplification reaction, it is important to ensure that respective amplification inhibitors that are released from the biological sample during lysis do not disturb the subsequent amplification. Suitable embodiments for compound (A) which provide both functions will be described in the following.

Preferably, compound (A) binds or otherwise complexes amplification inhibitors that are released from the biological sample, thereby allowing to deplete, respectively "inactivate", these inhibitors in the obtained lysate. However, as compound (A) itself is an inhibitor of the amplification reaction, it inhibits the amplification reaction if no sufficient (e.g. no or not enough) sample material was added for lysis. In this case, no or no sufficient amount of inhibitors is released during lysis and accordingly, cannot be bound or complexed by compound (A). In this case, compound (A) remains accessible or otherwise "free" during the amplification reaction in a concentration wherein it disturbs the amplification reaction so that no amplification signal is obtained. Without being bound in theory, it is believed that the inhibitory action of compound (A) on the amplification reaction is basically "neutralized" by the amplification inhibitors that are released from the biological sample during lysis. It is believed that compound (A) forms complexes or otherwise associates with the inhibitors that are released from the biological sample, wherein said interaction somehow eliminates or reduces the inhibitory action of both inhibitors (compound (A) and inhibitors released from the biological sample). However, if no sufficient biological sample material was added (which could result in a false negative result), the inhibitory activity of compound (A) (which is then not sufficiently "neutralized" by inhibitors released from the biological sample) prevails and compound (A) then inhibits the amplification reaction so that no amplification signal is obtained. Therefore, the amount of sample material to be processed and the concentration of compound (A) are adjusted such that the sample material and/or the inhibitors released therefrom during lysis reduces the inhibiting activity of compound (A) to such an extent that the amplification reaction can be performed if the lysate, respectively, a defined portion thereof, is subjected to the amplification reaction. By analysing whether the amplification reaction is inhibited, invalid amplification reactions (false negatives) that occur because no or no sufficient amount of sample material was subjected to the assay are identified and respective amplification reactions can be reported or sorted out as invalid.

Compound (A) preferably comprises at least one anionic group. Said at least one anionic group may be selected from the group consisting of carboxyl, sulfonate, sulphate, phosphonate and phosphate groups. Preferably, compound (A) comprises at least one carboxyl and/or sulfonate group. Compound (A) may be a betaine or sulfobetaine.

Preferably, compound (A) is selected from the group consisting of water-soluble polyanionic polymers which comprise carboxylate-containing monomers, anionic detergents and zwitterionic detergents. As is shown by the examples, respective compounds are well suitable for use as compound (A) because they deplete, e.g. complex, inhibitors released from the biological sample thereby improving the amplification reaction if sufficient biological sample material was added for lysis while they inhibit the amplification reaction if no or no sufficient amount of sample material was used for preparing the lysate because in this case no or not sufficient inhibitors originating from the biological sample are present in order to "neutralize" the inhibitory action of compound (A) on the amplification reaction. Thus, respective compounds are preferred for use as compound (A) because they have a dual function as described above. The concentration of compound (A) is adjusted to the amount of sample material to be processed and amount of lysate that is subjected to the amplification reaction to achieve this result. Suitable concentrations for individual settings can be determined by routine experiments following the teachings described herein.

According to one embodiment, compound (A) is a water-soluble polyanionic polymer comprising carboxylate groups, such as e.g. polyacrylic acid (poly(acrylic acid) or PAA). As shown in the examples, using a respective lysing procedure wherein a respective water-soluble polyanionic polymer comprising carboxylate groups is added in step a) provides a lysate that can be used directly in an amplification reaction. Inhibitors of amplification reactions originating from the biological sample are advantageously depleted due to the addition of the water-soluble polyanionic polymer, it is assumed by way of unspecific complex formation. Excellent results are achieved even if said polymer such as PAA is used alone in order to deplete inhibitors. Thus, the incorporation of the water-soluble polyanionic polymer comprising carboxylate groups during lysis has the effect—if the biological sample was validly added—that the amplification reaction shows an improved performance compared to if said polymer is not being used during lysis. However, respective water-soluble polyanionic polymers such as e.g. polyacrylic acid are themselves PCR inhibitors. Hence, that respective water-soluble polyanionic polymers comprising carboxylate groups such as polyacrylic acid can be used to reduce the inhibitory effect of PCR inhibitors released from the biological sample thereby improving the performance of the amplification reaction was itself highly unexpected. This dual function is now used in the present invention to provide a reliable control that the biological sample was added during lysate preparation. Because if no or no sufficient amount of biological sample was added, the inhibitory activity of said polymers on the amplification reaction prevails which has the effect that no amplification signal is obtained. However, if the biological sample was validly added, at least two advantageous effects are obtained. First, the inhibitory activity of the polymer is overcome due to the inhibitors that are released from the biological sample, thereby indicating that biological sample material was validly added and that the assay was performed accurately. In this case, additionally, the amplification reaction is improved, because inhibitors that are released from the biological sample are effectively depleted by the polymer, thereby improving the amplification reaction and allowing that the obtained lysate can be directly used—i.e. without intermediate nucleic acid isolation—in the amplification reaction.

Thus, when following the teachings of the present invention and adding a water-soluble polyanionic polymer comprising carboxylate groups during lysis of the biological sample, a lysate is provided that can be used without prior isolation of the nucleic acids in the nucleic acid amplification reaction and at the same time provides a reliable integrated control that sufficient sample material was added during lysis. The obtained lysate can even be added in rather large amounts into the amplification reaction. That a rather large amount of lysate can be transferred into the amplification reaction is a particular advantage, as thereby the sensitivity of the amplification can be improved because e.g. more nucleic acids are transferred with the lysate into the analytical method. This is a particular advantage for diagnostic applications.

Preference within the scope of the invention is given to water-soluble polyanionic polymers, including copolymers, comprising carboxylate-containing monomers, such as preferably comprising acrylic acid, methacrylic acid and/or maleic acid. According to one embodiment, said polymer that is used as compound (A) comprises only two types of monomers. Preferably, only one type of monomer is comprised in the water-soluble polyanionic polymer.

In a preferred embodiment, compound (A) is selected from polyacrylic acid, polymaleic acid and poly(acrylic acid-co-maleic acid). Most preferably, polyacrylic acid is used. As shown in the examples, polyacrylic acid is very efficient in inhibiting the amplification if no sufficient sample material was used during lysis while preventing an inhibition of the amplification reaction by depleting inhibitors that are released during lysis if the biological sample material was validly added during lysis.

If a copolymer is used as compound (A), it may additionally comprise polar monomers which do not contain carboxylate. Examples of respective polar monomers encompass lactide and/or vinylpyrrolidone. According to one embodiment, said polymer comprises only one type of the respective polar monomers. According to one embodiment the copolymer is poly(acrylic acid-co-lactide), poly(acrylic acid-co-vinylpyrrolidone), poly(maleic acid-co-lactide), poly(maleic acid-co-vinylpyrrolidone), poly(acrylic acid-co-maleic acid-co-lactide) or poly(acrylic acid-co-maleic acid-co-vinylpyrrolidone). Furthermore, the copolymer additionally may comprise anionic monomers not containing carboxylate. According to one embodiment, the copolymer is a block copolymer. Also a plurality of different compounds (A) such as a plurality of water-soluble polyanionic polymers comprising carboxylate groups can be used.

The molecular weight of the water-soluble polyanionic polymer is preferably chosen such that it is present in a solved form in the lysis mixture and preferably also in the aqueous lysis composition if comprised therein. The average molecular weight of the at least one water-soluble polyanionic polymer that can be used as compound (A) is preferably selected from a range of 2,000 Da to 500,000 Da, 5,000 Da to 475,000 Da, 10,000 to 450,000 Da, 25,000 to 400,000 Da, 35,000 to 350,000 Da, 50,000 Da to 300,000 Da, 75,000 to 300,000 Da, 100,000 Da to 300.000 Da, 150,000 to 300,000 Da and 200,000 Da to 275,000 Da. In a preferred embodiment the average molecular weight is approx. 250,000 Da.

As described above, the concentration of compound (A) and thus the water-soluble polyanionic polymer or mixture thereof in the lysate must be chosen such that, when the desired amount of the lysate is transferred into the amplification reaction, it inhibits the amplification reaction if no sufficient sample material was added for obtaining the lysate while it does not inhibit the amplification reaction if sufficient biological sample material was added for obtaining the lysate. The suitable concentration for the individual case can be determined by routine experiments following the teachings described herein. It is referred to the above disclosure for details.

According to one embodiment, the water-soluble polyanionic polymer or mixture of water-soluble polyanionic polymers used as compound (A) is comprised in the aqueous lysis composition in a concentration that is selected from 0.01% (w/v) to 1% (w/v), 0.02% (w/v) to 0.5% (w/v), 0.025% (w/v) to 0.3% (w/v), 0.035% (w/v) to 0.2% (w/v) and 0.04% (w/v) to 0.15% (w/v). Respective concentrations are particularly suitable when transferring rather large amounts of lysate into the amplification reaction, e.g. when using the lysate for reconstituting a dry reagent composition comprising amplification reagents as is described in the examples. Higher concentrations can be used if the lysate is diluted, e.g. by adding water, by additionally using water or another suitable solvent during reconstitution or by transferring only a small amount of lysate into an aqueous amplification reaction. The concentration of compound (A) in the lysate shall be such, that upon subjecting the desired amount of lysate to the amplification reaction, compound (A) is present in said amplification reaction in a concentration wherein it inhibits the amplification reaction if no sufficient sample material was added for obtaining the lysate while it does not inhibit the amplification reaction if sufficient biological sample material was added for obtaining the lysate. According to one embodiment, compound (A) is comprised in the aqueous lysis composition that is added to the sample in a concentration selected from 0.025% (w/v) to 0.15% (w/v), 0.03% (w/v) to 0.1% (w/v), 0.03% (w/v) to 0.075% (w/v) and 0.035% (w/v) to 0.05% (w/v). Respective concentrations are particularly suitable when using polyacrylic acid as compound (A) for reconstituting a dry reagent composition.

According to one embodiment, compound (A) is an anionic or zwitterionic detergent. It may be comprised in the lysis composition. As described above, the concentration of compound (A) and thus the anionic or zwitterionic detergent in the lysate must be chosen such that, when the desired amount of the lysate is transferred into the amplification reaction, it inhibits the amplification reaction if no sufficient sample material was added for obtaining the lysate while it does not inhibit the amplification reaction if sufficient biological sample material was added for obtaining the lysate. The suitable concentration for the individual case can be determined by routine experiments following the teachings described herein and depends in particular on the type of sample material, the amount of sample material to be processed and on the amount of lysate that is subjected to the amplification reaction. It is referred to the above disclosure for details. Suitable concentrations may be selected from 0.01% (w/v) to 5% (w/v), 0.05% (w/v) to 2% (w/v), 0.075% (w/v) to 1% (w/v) and 0.1% (w/v) to 0.5% (w/v). Respective concentrations are particularly suitable when transferring rather large amounts of lysate into the amplification reaction, e.g. when using the lysate for reconstitution of a dry reagent composition comprising amplification reagents as is described in the examples. Higher concentrations can be used if the lysate is diluted, e.g. by adding water, by additionally using water or another suitable solvent during reconstitution or by transferring only a small amount of lysate into an aqueous amplification reaction as was also described above. Using a respective detergent as compound (A) is advantageous, because said detergent also assists the lysis of the biological sample material. Preferably, said detergent comprises a sulfonate group. According to one embodiment, it is a betaine, preferably a sulfobetaine. It may be a tetradecyl derivative. According to one embodiment, the composition used for preparing the lysate comprises 3-(N,N-Dimethylmyristylammonio)propanesulfonate (Sulfobetain 3-14; SB3-14; CAS No. 14933-09-6). As is shown by the examples, said compound is very suitable for use as compound (A) in the present invention. A respective detergent can also be used in combination with another compound (A), e.g. the water-soluble polyanionic polymer described above.

Compound (A) is comprised in a composition that is used for preparing the lysate. Thus, said composition is added during lysis and accordingly, is comprised in the obtained lysate that is then subjected to the amplification reaction. Preferably, said composition is an aqueous composition.

According to a preferred embodiment, compound (A) is comprised in a lysis composition that is used for lysing the biological sample. In certain embodiments, said lysis composition is also used as sample collection medium.

According to a preferred embodiment, the lysis composition used for preparing the lysate is an aqueous lysis composition. Said lysis composition preferably comprises a detergent. Detergents support the lysis of the sample and dissolve protein aggregates. Also, a mixture of detergents can be used. According to one embodiment, compound (A) is a detergent as described above. In this case, compound (A) additionally provides the function of the detergent and assists the lysis. In this case, an additional detergent may or may not be used which also depends on the sample to be processed.

According to one embodiment, a non-ionic detergent or a combination of non-ionic detergents are comprised in the aqueous lysis composition. According to one embodiment, the aqueous lysis composition and also the lysis mixture comprises only non-ionic detergent(s). Substances which are suitable for this purpose are, in principle, any non-ionic surfactant which allows performing the subsequent nucleic acid analysis method with the obtained lysate in case the sample was validly added. The non-ionic surfactant may be selected from the group consisting of polyoxyethylene fatty alcohol ethers, polyoxyethylene alkylphenyl ethers, polyoxyethylene-polyoxypropylene block copolymers, polysorbates and alkylphenol ethoxylates, preferably polyoxyethylene fatty alcohol ethers, polysorbates and/or polyoxyethylene alkyl-phenyl ethers.

The term "fatty alcohol" in particular means for the purposes of the present invention alcohols having a chain length of from 6 to 22 carbon atoms, preferably 8 to 20 carbon atoms, preferentially 10 to 18 carbon atoms, particularly preferably 12 to 18 carbon atoms. Preference is in particular given to alcohols having 12, 14, 16 or 18 carbon atoms. Although the fatty alcohols may be mono- or poly-unsaturated, they are preferably saturated fatty alcohols. The term "polyoxyethylene" in particular means for the purposes of the present invention an HO—(CH2CH2O)n unit, with n being preferably an integer from 2 to 150, further preferably from 4 to 120, still further preferably from 8 to 80, and most preferably an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

Preferred examples of suitable polyoxyethylene fatty alcohol ethers are polyethoxylated lauryl, cetyl, oleyl, or stearyl alcohols which may be used alone or as mixture. According to a preferred embodiment of the invention, the at least one polyoxyethylene fatty alcohol ether comprises a fatty alcohol moiety having from 6 to 22 carbon atoms and a polyoxyethylene moiety having from 2 to 150 ($CH_2CH_2O$) units. Preferably, the polyoxyethylene fatty alcohol ether is selected from the group consisting of polyoxyethylene lauryl ether, polyoxyethylene cetyl ether (Brij-58), polyoxyethylene stearyl ether and/or polyoxyethylene oleyl ether.

As alkylglucoside, preferably a non-ionic surfactant from the group of the polysorbates, preferably polysorbate 20 (Tween 20), polysorbate 40 or polysorbate 80, more preferred polysorbate 20 is used.

Preferred examples of polyoxyethylene alkyl phenyl ethers include nonylphenol ethoxylates (Tergitol), polyethylene glycol p-(1,1,3,3-tetramethylbutyl)-phenyl ether (Triton X-100) and nonylphenylpolyethylenglycol (Nonidet P-40).

According to one embodiment, at least two non-ionic detergents are used in combination. Preferably, an alkylglucoside, preferably a polysorbate, and a polyoxyethylene alkyl phenyl ether are used in combination.

According to one embodiment, the non-ionic detergent is selected from the group consisting of polysorbate 20 (Tween 20), Tergitol, Triton X-100, Brij-58 and Nonidet P-40. Preferably, at least two respective non-ionic detergents are comprised in the aqueous lysis composition.

The concentration of the non-ionic detergent or the combination of non-ionic detergents in a respective lysis composition is preferably selected from 0.05% (v/v) to 5% (v/v), 0.1% (v/v) to 3% (v/v), 0.15% (v/v) to 2.5% (v/v), 0.2% (v/v) to 2% (v/v), 0.3% (v/v) to 1.5% (v/v) and 0.4% (v/v) to 1% (v/v). Preferably, Tween 20 and/or Nonidet P-40, preferably a combination of both, are comprised in the aqueous lysis composition. Preferably, the overall concentration of non-ionic detergent(s) or all detergents in the lysis mixture is ≤5%, preferably ≤3% (v/v), more preferably ≤2% (v/v).

Preferably, the aqueous lysis composition comprises at least one buffering agent. The buffering agent should be capable of buffering the aqueous lysis composition and preferably also the obtained lysate at a pH range that is compatible with the pH range that is required for performing the subsequent analytical method, such as e.g. an amplification reaction. This, as the pH of the lysate is strongly affected by the aqueous composition that is used for lysis and the lysate is directly used in the subsequent analytical method without prior purification of the nucleic acids. Preferably, a buffering agent is used in the aqueous lysis composition so that the pH of the composition is in a range selected from 7 to 11, 7.5 to 10, 7.75 to 9.5 and 8.0 to 9.

Furthermore, preferably, also the obtained lysate has a pH value that lies in said range. Respectively, buffered aqueous lysis compositions are particularly suitable for providing a lysate that is suitable for performing a nucleic acid amplification reaction.

The buffering agent can be comprised in the aqueous lysis composition in a concentration selected from 5 mM to 150 mM, 7.5 mM to 125 mM, 10 mM to 100, 10 mM to 80 mM and 10 mM to 50 mM. Preferably, the buffer substance is selected from the group consisting of Tris, MOPS, HEPES, phosphate and borate, more preferred selected from Tris and borate.

According to one embodiment, the lysis composition comprises at least one chelating agent, which preferably is suitable for chelating divalent cations. Respective chelating agents are suitable for protecting nucleic acids from degradation. Suitable chelating agents include but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2EDTA$, $K_3EDTA$ or $Na_2EDTA$. Using a chelating agent such as EDTA has the advantageous effect that nucleases such as DNases and RNases are inhibited. According to one embodiment, the chelating agent is comprised in the aqueous lysis composition. The chelating agent preferably is employed in a concentration of 0.5 mM to 5 mM, preferably 0.75 mM to 2 mM, most preferred 1 mM to 1.5 mM in the aqueous lysis composition. Preferably, EDTA is used.

Further additives can be incorporated into the lysis mixture and/or the lysis composition. E.g. additives can be used that protect the released nucleic acids from degradation. E.g. suitable DNase and/or RNase inhibitors can be added. The incorporation of RNase inhibitors is particularly recommended if RNA is the nucleic acid of interest as RNA is very susceptible to degradation. Suitable protective agents are known in the prior art and, thus, do not need any detailed description here. As the lysed sample is directly subjected to the amplification reaction, it is important to ensure that the performed lysis does not result in a lysate which comprises one or more amplification inhibitors in a concentration that would inhibit the performance of the amplification.

As described above, the compounds (A) described above such as preferably PAA and SB3-14 deplete inhibitors that are released during lysis of the biological sample. They can be used alone in order to deplete amplification inhibitors that are released from the biological sample. However, if desired, further additives can be added, respectively can be included during lysis, that also prevent or reduce an inhibition of the amplification by depleting inhibitors that are released from the biological sample during lysis. Also, more than one additive can be used for said purpose. Using additional compounds for depleting inhibitors can be advantageous e.g. when processing inhibitor-rich samples or specific sample types. Thereby, the amplification result can be improved. According to one embodiment, said further additive that prevents or reduces an inhibition of the subsequent amplification reaction by depleting inhibitors, does itself not inhibit the amplification reaction in the used concentration irrespective of whether the biological sample was added during lysis or not. Thereby, a respective additive can be distinguished from a compound (A) in the sense of the present invention. Furthermore, respective additional additives are used in a concentration wherein they do not disturb the function of compound (A). When using such additional compound which also depletes, respectively "inactivates" inhibitors that are released from the sample, less inhibitors are available for interaction with compound (A), if compound (A) also binds inhibitors released from the biological sample as is described above. In such case it must be ensured that the concentration of compound (A) in the lysate is still chosen such that, when the desired amount of the lysate is transferred into the amplification reaction, compound (A) does not inhibit the amplification reaction if sufficient biological sample material was added for obtaining the lysate. Therefore, if additional inhibitor depleting compounds are used, the concentration of compound (A) might need to be adjusted. As described above, the suitable concentrations for the individual case can be determined by routine experiments following the teachings described herein.

According to one embodiment, a polymer is additionally used for depleting inhibitors that act as a binder and/or thickener. Said binder and/or thickener is preferably water-soluble and is incorporated into the aqueous lysis composition. It may be selected from the group consisting of polyvinylpyrrolidone (PVP), polyoxazoline, polyethylene glycol, polyvinyl alcohol and Luvitec. Said polymer can be comprised in the aqueous lysis composition in a concentration that is selected from 0.01% (w/v) to 1% (w/v), 0.02% (w/v) to 0.5% (w/v), 0.025% (w/v) to 0.3% (w/v), 0.035% (w/v) to 0.2% (w/v) and 0.04% (w/v) to 0.15% (w/v). Preferably, it is comprised therein in a concentration selected from 0.05% (w/v) to 0.15% (w/v) and 0.075% (w/v) to 0.125% (w/v). According to one embodiment, polyvinylpyrrolidone is used as further additive and preferably, is incorporated into the aqueous lysis composition in said concentrations. Suitable binders and/or thickeners that can be used for depleting inhibitors are also described in WO 2010/003493.

According to one embodiment, inhibitors of the subsequent amplification method are depleted by binding inhibitors to a solid support which has an anionic surface. As described above, respective inhibitors in particular originate from the biological sample during lysis. Said solid support having an anionic surface can be additionally used, thereby improving the amplification result. The solid support comprises an anionic surface which binds to inhibitors that are released during lysis. The term "binding" is used in a broad sense and refers to any interaction or association of the inhibitors with the solid support. Binding preferably is achieved by adsorption. By binding the inhibitors to the solid support, they are depleted from the lysate and the subsequent amplification reaction can be performed directly using the obtained lysate. Thereby, the depletion performance can be improved which is an advantage for samples which comprise large amounts of inhibitors. However, as described above, in such case wherein less inhibitors might be available for interaction with compound (A) it must be ensured that the concentration of compound (A) in the lysate is still chosen such that, when the desired amount of the lysate is transferred into the amplification reaction, compound (A) does not inhibit the amplification reaction if sufficient biological sample material was added for obtaining the lysate.

It is preferred to separate the solid support with the bound inhibitors from the lysate. Thereby, it is ensured that inhibitors are not again released during the subsequent handling and/or during the performance of the subsequent nucleic acid analysis method. Using a respective solid support having an anionic surface for binding amplification inhibitors may be advantageous as it allows to also clear the lysate at the same time. It was found that anionic surfaces which bind to inhibitors such as in particular PCR inhibitors also bind precipitates that may form during the lysis of the biological sample. Thus, respective precipitates which may also comprise or consists of inhibitors can also be removed when using a respective solid support. Thus, according to one embodiment, a respective solid support having an anionic surface is used even if compound (A) and/or other additives used for obtaining the lysate are alone sufficient to deplete inhibitors released from the biological sample. Further details regarding the lysate clearing are also described subsequently.

The term "surface" as used herein in particular refers to a portion of a solid support which comes into contact with a liquid when the solid support is contacted therewith. The solid support provides an anionic surface that allows to bind amplification inhibitors. For this purpose, it is also within the scope of the present invention to functionalize the surface of a solid support with appropriate functional groups. Suitable examples will be described below. E.g. the solid support and/or its surface may comprise or consist of a polymer capable of forming an anionic structure. E.g. the polyanionic polymer, which may also be a copolymer or terpolymer, may be a polycarboxylate or a carboxylated polymer or a polyester capable of forming an anionic structure. According to one embodiment, said polymer is a carboxylated polymer e.g. based on vinyl methyl ether, maleic anhydride, styrene, linear or branched alkenes or acrylic acid and its derivatives. For example, polymers based on styrene, vinyl methyl ether, linear or branched alkenes-such as e.g. 1-octadecene or isoprene and maleic acid or acrylic acid, wherein the carboxyl functionalities can be optionally esterified to different degrees, can be employed. Preferred exemplary acrylic acid alkyl esters include the following: methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl acrylate, 2-ethylhexyl methacrylate, phenyl methacrylate, octyl methacrylate, decyl methacrylate, dodecyl methacrylate, myristyl methacrylate, lauryl methacrylate, cetyl methacrylate, where the acrylic acid methyl ester is particularly preferred. Polyesters that are capable of forming an anionic structure illustrate further suitable polymers. In general, the monomers themselves can possess groups that after polymerisation constitute or form anionic sites.

Moreover, the polyesters can also be subsequently provided with groups forming anions, e.g. through unsaturated sites or other functional groups present in the polyester. Dicarboxylic acids, such as succinic acid, adipic acid, phthalic acid or maleic acid, and as alcohols, tartaric acid or other dihydric or trihydric alcohols that comprise at least one additional anionic functionality, are preferably used as the monomers. When maleic acid is used as the monomer, dihydric or trihydric alcohols—without additional anionic functionalities—can be used for the polymerisation, when the residual double bond of the maleic acid in the polymer is utilized, for example, to subsequently introduce anion forming groups, such as for example acrylic acid or methacrylic acid. In principle, all anionic structures formed from polymers are suitable to provide the surface of the solid support, with carboxylated polymers being preferred. Respective polymers may also form a coating on a solid support, thereby providing an appropriate anionic surface for binding inhibitors. Furthermore, the solid support may comprise iminodiacetic acid groups.

It is preferred that the anionic surface comprises multiple acidic functional groups and thus provides a polyanionic surface. According to one embodiment, the pKa value of said functional groups lies in a range of 0 to 7, preferably 1 to 6, more preferred 1 to 5. Suitable examples include acidic groups such as carboxyl groups. Further suitable functional groups include sulfonate, phosphonate and phosphate groups. Also, mixtures of respective functional groups can be present on the surface. Preferably, the surface comprises carboxyl groups as functional groups, as a respective carboxylated surface is highly efficient in binding and thus depleting amplification inhibitors and additionally, allows to bind precipitates that may be formed during lysis thereby additionally providing a lysate clearing effect if desired. The manufacture of carboxylated polymers is well known from the prior art as these polymers are employed in a great number of other technical applications, they are for the most part commercially available. Furthermore, it is also well known how to provide and e.g. functionalize a solid support with a respective anionic surface, preferably a carboxylated surface. Examples include, but are not limited to, coatings, the deposition of a film or layer and the manufacture of the solid support by anionic polymers. As described above, the anionic functional groups can be provided by the surface material itself, e.g. acidic groups such as carboxyl groups (e.g. if the surface is made of a polyacrylate) or respective functional groups can be provided by ligands or polymers that are attached to or are provided covalently or non-covalently to the surface of the solid support.

Suitable solid supports may be made of or may comprise in particular at their surface a material selected from the following group
- a material comprising or consisting of silicon such as silica and polysilicic acid materials, quartz, borosilicates, silicates, diatomaceous earth or glasses,
- a material comprising or consisting of an organic or inorganic polymer such as poly(meth)acrylate, polyurethane, polystyrene, polystyrol, polyacrylamide, a divinylbenzene polymer, a styrene divinylbenzene polymer, polyethylene, polypropylene, polyvinylidene fluoride, polyacrylonitrile, polyvinylchloride, polyacrylate, polyacrylamide, polymethacrylate or a methyl methacrylate polymer;
- a material comprising or consisting of a polysaccharide such as agarose, cellulose, dextrans or sepharose;
- a material comprising or consisting of a mineral;
- a material comprising or consisting of a metal oxide such as aluminum oxide, magnesium oxide, titanium oxide or zirconium oxide;
- a material comprising or consisting of a metal such as gold or platinum; and
- a material comprising or consisting of a derivative of the foregoing.

Also, any solid support suitable for anion exchange chromatography may be used as solid support to provide an anionic surface that allows to bind, if necessary after appropriate functionalization, amplification inhibitors released from the biological sample. Exemplary polymeric materials that provide, or can be modified to provide acidic groups such as carboxyl groups include, for example, polymers such as polystyrene, latex polymers (e.g., polycarboxylate coated latex), polyacrylamide, polyethylene oxide, polyacrylate and derivatives thereof.

Preferred formats of the solid support include but are not limited to particles such as beads, membranes, filters, plates, columns, vessels and dipsticks. According to one embodiment, the anionic surface which binds inhibitors is provided by a vessel, for example the inner surface of a vessel that is used to receive the fixed sample and for performing the lysis. The inner surface of the surface or portions thereof can be functionalized, e.g. coated, with suitable ligands, e.g. carboxylated ligands or anionic polymers. Examples of respective vessels that can be respectively functionalized include but are not limited to microtubes and wells of a microplate. In this embodiment, the inhibitors released from the biological sample bind to the inner surface of the vessel and are thereby depleted from the lysate. When removing the lysate from said vessel, the bound inhibitors remain in the vessel and are thereby separated from the lysate.

According to a preferred embodiment, the anionic surface is provided by a solid support that can be provided as suspension and can be separated from a liquid phase. Preferably, the surface which binds inhibitors is provided by particles. Preferably, particles having a carboxylated surface are used. The particles may have an average size that is selected from a range of 100 nm to 50 µm, 200 nm to 40 µm, 300 nm to 35 µm, 400 nm to 30 µm, 450 nm to 25 µm, 500 nm to 20 µm, 550 nm to 15 µm, 600 nm to 12.5 µm, 650 nm to 10 µm, 700 nm to 7.5 µm, 750 nm to 5 µm, 800 nm to 3.5 µm, 800 nm to 3 µm, 800 to 2.5 µm, 800 nm to 2 µm and 800 nm to 1.5 µm. Particles of the respective sizes and in particular of a smaller size such as 10 µm or less, 7.5 µm or less, preferably 5 µm or less, 2.5 µm or less or 1.5 µm or less are easy to handle and can be well resuspended in the lysis mixture. Furthermore, respective small particles provide a large surface area that can bind and accordingly can efficiently deplete inhibitors and other contaminants such as precipitates originating from the biological sample from the lysate. Suitable materials for providing or making the particles and for providing an anionic surface are described above. The particles may also comprise more than one of the above described materials, e.g. comprising two or more layers comprising or consisting of different materials to provide the particle body.

If the particles are non-magnetic, they can be collected for example by filtration or sedimentation which can according to one embodiment be assisted by centrifugation. It is preferred though to use magnetic particles, because magnetic particles including the bound inhibitors and precipitates can be processed easily by the aid of a magnetic field, e.g. by using a permanent magnet. This embodiment is preferred as it is compatible with established systems capable of processing magnetic particles and is also suitable for automation. Here, different systems exist in the prior art that can be used in conjunction with the present invention to process magnetic particles having an anionic surface to which inhibitors and optionally precipitates originating from the biological sample were bound. According to one embodiment, the magnetic particles with the bound inhibitors are collected at the bottom or the side of the reaction vessel. Thereby, bound inhibitors are depleted from the lysate and concentrated at the bottom or side of the reaction vessel. The remaining liquid sample can then be removed from the reaction vessel. Removal can occur e.g. by aspiration. Such systems are well known in the prior art and thus need no detailed description here. In an alternative system that is known for processing magnetic particles, a magnet which is usually covered by a cover or envelope plunges into the reaction vessel to collect the magnetic particles. The magnetic particles carrying the bound inhibitors and optionally precipitates can then be removed, leaving behind an inhibitor depleted lysate. As respective systems are well-known in the prior art and are also commercially available (e.g. QIASYMPHONY®; QIAGEN), they do not need any detailed description here. In a further alternative system that is known for processing magnetic particles, the lysate including the magnetic particles can be aspirated into a pipette tip and the magnetic particles can be collected in the pipette tip by applying a magnet e.g. to the side of the pipette tip. The remaining sample which corresponds to the inhibitor depleted lysate can then be released from the pipette tip while the collected magnet particles which carry the bound inhibitors and precipitates remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

The magnetic particles can for example have superparamagnetic, paramagnetic, ferrimagnetic or ferromagnetic characteristics. Preferably, superparamagnetic particles are used. The magnetic particles may comprise a magnetic material that is incorporated in the particles and/or is associated with the particles. To avoid leaching of the magnetic material, the magnetic material is preferably completely encapsulated. The magnetic material may provide the core(s) of the particles, may be comprised in the core and/or may be applied onto the core of the particle.

According to one embodiment, the particle comprises a polymer core e.g. made of polystyrol, which is surrounded by at least one polymeric layer, preferably at least two polymeric layers, preferably a polyethylenimine layer and/or a polyacrylate layer. Preferably, the particle surface is made of or comprises a polyacrylate. Thereby, carboxyl groups are provided at the surface of the particle. Carboxyl groups are very effective in binding inhibitors, such as PCR inhibitors released from the biological sample and are also very effective in binding precipitates that may form during lysis. Thereby, inhibitors and optionally precipitates can be depleted from the lysate. If magnetic particles are used, a magnetic material such as e.g. iron oxide can be deposited on the polystyrol core. Afterwards, at least one, preferably at least two polymeric layers as described above are applied and the surface of the obtained magnetic particle provides functional groups suitable for binding inhibitors, such as e.g. carboxyl groups.

For functionalizing a surface with anionic functional groups that can bind inhibitors, several methods are feasible. The functional groups, respectively compounds comprising respective groups may be bound directly to the surface, either covalently or non-covalently, electrostatically and/or may form part of a polymer or other composition which forms a surface coating or which is provided at the surface of the solid support. Also, precipitation based approaches are feasible. According to one embodiment, the functional groups such as preferably carboxyl groups are provided in form of a coating on the solid support. According to one embodiment, a covalent coupling strategy is used. Suitable methods for providing functional groups such as carboxyl groups on the surface of a solid support are well known to the skilled person and thus, do not need any specific description herein. The respective carboxyl groups are preferably provided by a polyacrylate layer or another polyanionic polymer which comprises carboxyl groups. Suitable examples were described above.

When following the teachings described herein, binding of inhibitors released from the biological sample to the anionic surface of the solid support occurs under conditions wherein the inhibitors bind to the surface but wherein the nucleic acids of interest do not or bind to a lesser extent. Hence, the used lysis conditions are selective in that predominantly inhibitors released from the biological sample bind to the solid support, respectively its anionic surface, but wherein no substantial binding of the nucleic acids of interest occurs, so that the nucleic acids remain in a sufficient amount in the lysate to allow performing the intended amplification reaction. As described above, preferably, a solid support having a carboxylated surface is used. Most preferred, magnetic particles having a carboxylated surface are used. According to one embodiment, the solid support having an anionic surface, in particular a carboxylated surface that is used for binding inhibitors released from the biological sample is present during lysis. Thereby, it is ensured that inhibitors that are released upon lysis of the biological sample are directly bound to the anionic surface of the solid support upon their release and thus are efficiently depleted from the remaining sample. This improves the depletion of the inhibitors. Clearing of the lysate as will be described subsequently may further improve the results of the amplification reaction. If using a solid support having an anionic surface, also precipitates formed during lysis will bind to the anionic surface. Thus, as described, the lysate can not only be depleted from PCR inhibitors released during lysis of the biological sample but can also be depleted from precipitates. The solid support having an anionic surface for binding inhibitors and optionally precipitates may be comprised in the aqueous lysis composition. As described above, preferably, a solid support having a carboxylated surface is used. Most preferred, magnetic particles having a carboxylated surface are used.

Other additives that can be additionally used to deplete inhibitors released from the biological sample include but are not limited to non-ionic resins that adsorb ionic species through hydrophobic and polar interactions such as e.g. Amberlite XAD-7.

A particularly preferred aqueous lysis composition comprises or consists of
- at least one compound (A), which is a water-soluble polyanionic polymer as described above, preferably polyacrylic acid, in a concentration of 0.01% (w/v) to 0.5% (w/v), preferably 0.02% (w/v) to 0.2% (w/v), more preferred 0.03% (w/v) to 0.15% (w/v);
- optionally at least one binder and/or thickener suitable for depleting inhibitors released from a biological sample during lysis;
- at least one non-ionic detergent, preferably at least two non-ionic detergents, preferably Polysorbate 20 (Tween 20) and nonylphenylpolyethylenglycol (Nonidet P40), wherein each non-ionic detergent is comprised in a concentration of 0.2% (v/v) to 0.6% (v/v), preferably 0.4% (v/v) to 0.5% (v/v);
- a buffering agent, preferably TRIS or borate,
- optionally a chelating agent in a concentration 2 mM, preferably 1.5 mM.

The pH value of the respective aqueous lysis composition preferably lies in a range of 7.5 to to 9.5, 8.0 to 9 or 8.5 to 9.

A further particularly preferred aqueous lysis composition comprises or consists of
- at least one compound (A), which is an anionic or zwitterionic detergent comprising a sulfonate group, preferably 3-(N,N-Dimethylmyristylammonio)propanesulfonate (Sulfobetain 3-14), in a concentration of 0.01% (w/v) to 0.5% (w/v), preferably 0.05% (w/v) to 0.3% (w/v), more preferred 0.1% (w/v) to 0.2% (w/v);
- optionally a proteolytic enzyme;

a buffering agent, preferably TRIS, optionally a chelating agent in a concentration 2 mM, preferably 1.5 mM.

The pH value of the respective aqueous lysis composition preferably lies in a range of 7.5 to to 9.5, 8.0 to 9 or 8.5 to 9.

As is shown by the examples, respective aqueous lysis compositions are in particular compatible for providing a lysate that is suitable for direct use in an amplification reaction such as a PCR. As is shown in the examples, these lysis compositions achieve in combination with a heating step an efficient lysis of the biological sample and furthermore, do not comprise additives in a concentration that would substantially inhibit a respective amplification reaction if the sample was added during lysis. Therefore, lysates are provided which can be directly used in nucleic acid analysis methods such as amplification based analytical methods. However, if no or not enough biological sample material was added during lysis, the amplification reaction is inhibited thereby indicating that a false negative signal was obtained. The respective aqueous lysis compositions may also be used in combination with a solid support having an anionic surface as described above.

The term "lysis" as used herein refers to the disruption, degradation and/or digestion of the biological sample. In a respective lysis step, nucleic acids can be released from cells or can be freed from other sample components such as e.g. proteins. Herein, it is referred to a respective step to disrupt, degrade and/or digest a biological sample generally as lysis step, irrespective of whether nucleic acids are released from cells or whether the lysis is performed in order to release nucleic acids e.g. from proteins or other substances comprised in the biological sample, which may also be a cell-free or cell depleted sample such as plasma. Several methods are known in the prior art that allow to achieve an efficient lysis of different sample materials. Suitable lysis methods include but are not limited to mechanical, chemical, physical or enzymatic actions on the sample. Examples of respective lysis steps include but are not limited to grinding the sample in a bead mill, sonication, surface acoustic waves (SAW), repeated cycles of freezing and thawing, heating, the addition of detergents and/or the addition of protein degrading compounds such as e.g. protein degrading enzymes, e.g. hydrolases or proteases or salts. According to one embodiment, a protein degrading compound is used during lysis. The protein-degrading compound preferably is a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine proteases that have broad substrate specificities. Exemplary subtilisins include, but are not limited to, proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K. Preferably, the proteolytic enzyme is used under heating and/or agitation. Furthermore, one or more cell wall digesting enzymes can be used for lysis such as e.g. lysozyme, zymolase and/or pektinases. As the obtained lysate is directly used in the amplification reaction it is important to ensure that the obtained lysate is suitable for direct use in an amplification reaction. Thus, any additives that are used for lysis should not be used in a concentration wherein they would inhibit the performance of the amplification to an extent that the amplification cannot be adequately performed. The tolerable concentration also depends on the sensitivity that is required for the adequate performance of the analytical methods. These parameters can also vary from sample to sample. Furthermore, poteolytic enzymes used during lysis should be inactivated prior to subjecting the lysate to the amplification, e.g. by performing a heating inactivation step.

According to a preferred embodiment, lysis is assisted by heating the lysis mixture that is obtained by contacting the biological sample material with the lysis composition at ≥85° C. to provide a lysate. A respective heating step assists the lysis and ensures an efficient release of the comprised nucleic acids. Preferably, the lysis mixture is heated at ≥90° C., preferably ≥95° C. Such a heating step is also referred to as boiling lysis. At such high temperatures, enzymes that can optionally be used during lysis such as e.g. proteolytic enzymes and furthermore also nucleases get also denatured. The heat incubation type also depends on the biological sample to be lysed. E.g. fixed biological samples require a longer incubation time than non-fixed biological samples. Preferably, the lysis mixture is heated for at least 3 min, at least 5 min, at least 7.5 min, at least 10 min, at least 12.5 min, at least 15 min, at least 17.5 min, at least 20 min, at least 22.5 min, at least 25 min, at least 27.5 min or at least 30 min. Suitable heating periods may be selected from 3 min to 45 min, 5 min to 42.5 min, 7.5 min to 40 min, 12.5 min to 37.5 min and 15 min to 35 min. As is shown in the examples, the method according to the present invention allows to lyse the biological sample and to release the comprised nucleic acids from different biological samples thereby rendering the nucleic acids accessible for reverse transcription and amplification. Furthermore, as it is ensured that potential inhibitors are efficiently depleted, the obtained lysate can be directly used in the amplification reaction without prior purification of the nucleic acids. If the lysate was obtained using a biological sample, a positive amplification signal is obtained. If no or no sufficient amount of sample material was added, the amplification is inhibited due to the presence of compound (A), thereby indicating that the test was not accurately performed.

Preferably, after the heat incubation step, the heated sample is allowed to cool down. It may be cooled at room temperature or below. Preferably, it is allowed to cool down to a temperature below 50° C., more preferably it is cooled down at least to room temperature. It was found that a respective cooling step may—depending on the processed sample—promote the formation of precipitates. Said precipitates can be removed by clearing the lysate. Several options exist to clear the lysed sample. Non-limiting examples will be described below. A respective clearing step is advantageous to remove and/or inactivate precipitates that may depending on the processed sample be comprised in the lysate. However, as is shown by the presented examples, a respective clearing step is not necessarily required.

According to one embodiment, means are provided prior to, during or after lysis for removing contaminants, in particular precipitates that my have formed during lysis or debris, thereby providing a cleared lysate. The term "removing" as used in this conjunction means that the amount of precipitates is at least reduced or otherwise inactivated to an extent that the subsequent analytical method can be adequately performed. According to one embodiment, at least a portion of the lysate is passed through means that can hold back or remove precipitates and/or other solid contaminants during passage of the lysed sample. Suitable means may be selected from the group comprising filter materials, membranes or layers or fillings of particles. The lysate may pass through said means and precipitates and/or other contaminants are caught, respectively are held back by said means thereby providing a cleared sample once the sample has passed said means. Said means such as e.g. a filter or membrane may be porous. The pores should be sufficiently small to efficiently hold back and thus remove precipitates that are present in the lysis mixture. Said means should not substantially bind or hold back nucleic acids.

One source of contaminants, in particular when processing samples which comprises large amounts of cells, may be the formation of precipitates during lysis. Respective precipitates are in particular formed when processing certain sample types if lysis is assisted by a heating step. The carry-over of precipitates from the lysate into the amplification reaction can disturb the amplification and/or the interpretation of the obtained results and is thus not desired. Therefore, it is advantageous to separate precipitates from the remaining lysate in order to provide a cleared lysate. Separation can be assisted e.g. by sedimentation or centrifugation. The precipitates may e.g. sediment at the bottom of the tube, leaving behind a supernatant which corresponds to the cleared lysate which can then be used in the analytical method such as e.g. a reverse transcription and/or amplification reaction. Sedimentation can be accelerated and improved e.g. by centrifugation. However, it is preferred to assist the separation of the precipitates and to separate at least a portion of the precipitates from the lysate prior to using the cleared lysate in a nucleic acid analysis method.

According to one embodiment, precipitates formed are bound to a solid support having an appropriate surface for binding precipitates. As described above, a solid support having an anionic surface, in particular a carboxylated surface, can be used for that purpose. Preferably, the solid support is present during lysis. Thereby, it is ensured that inhibitors that are released upon lysis of the biological sample and formed precipitates are directly bound to the anionic surface of the solid support upon their release and/or formation and thus are efficiently depleted from the remaining sample. If using a solid support having an anionic surface, precipitates formed during lysis will bind to the anionic surface. Thus, as described, the lysate can not only be depleted from PCR inhibitors but can also be depleted from precipitates that may be present in the lysate. The solid support having an anionic surface for binding inhibitors and precipitates may also be comprised in the aqueous lysis composition. As described above, preferably, a solid support having a carboxylated surface is used. Most preferred, magnetic particles having a carboxylated surface are used.

The bound inhibitors and precipitates can be concentrated at the bottom of a vessel and the supernatant, which corresponds to the cleared lysate, can be obtained. Binding the precipitates to the solid support assists the sedimentation and hence alleviates the removal of the precipitates from the remaining sample. However, the addition of the solid support is also beneficial and provides a clearing effect in that the inhibitory effect of comprised contaminants such as precipitates is reduced, if the bound precipitates are not separated from the lysate but hence, are present during the analytical method. Apparently, complexing the precipitates by binding them to the solid support already provides a beneficial effect, apparently because the bound precipitates are not sufficiently accessible and hence are sufficiently inactivated in that they do not severely disturb the amplification. As described above, it is preferred to use a solid support having an anionic surface, preferably having a carboxylated surface. Respective solid supports allow to bind and thus allow to deplete inhibitors as well as precipitates that originate from the biological sample.

According to one embodiment, the solid support used for lysate clearing comprises or is a molecular sieve. A molecular sieve is a material containing small pores of a precise and uniform size that may be used as an adsorbent. Preferably, the molecular sieve comprises aluminosilicate minerals, clays, porous glasses, microporous charcoals, zeolites, active carbons, or synthetic compounds that have open structures through which small molecules, such as water can diffuse. Molecular sieves such as zeolites are particularly effective in removing contaminants such as precipitates from a lysate. The molecular sieve may be added to the aqueous lysis composition which preferably is a lysis solution. They may also be used in addition to the solid supports having an anionic surface described above. When processing acidic samples, such as vaginal swab samples, using a molecular sieve such as a zeolite as solid support has the specific advantage that zeolites are capable of elevating the pH value of the lysed sample and/or the lysis mixture. This is beneficial because usually, amplification reactions do not work properly at acidic pH values. This problem can be overcome when incorporating zeolites during the preparation of lysis mixture and in particular during preparation of a cleared lysate. E.g. the addition of zeolites allows to elevate the pH value from an acidic pH value to a pH value between 7 and 9.5, preferably 7.5 to 9, thereby additionally improving the performance of the amplification reaction such as a PCR which requires a pH value in a respective range. Hence, according to one embodiment, at least one type of solid support is added prior, during or after lysis of the biological sample which has the effect that the pH value of the lysed sample is elevated. This embodiment is particularly suitable when processing acidic biological samples such as vaginal swab samples having a pH below 7, below 6.5, below 6, below 5.5, below 5 or below 4.5. Preferably, a molecular sieve, more preferred zeolites, are used for this purpose. The molecular sieve can also be added in addition to other solid supports that bind inhibitors and/or precipitates such as carboxylated particles or other carboxylated solid supports.

According to one embodiment, the lysate is not cleared prior to performing the amplification reaction.

The term "biological sample" is used herein in a broad sense and is intended to include biological sources that contain nucleic acids. Exemplary biological samples include, but are not limited to, body fluids in general, whole blood, serum, plasma, red blood cells, white blood cells, buffy coat, swabs, including but not limited to buccal swabs, throat swabs, vaginal swabs, urethral swabs, cervical swabs, rectal swabs, lesion swabs, abcess swabs, nasopharyngeal swabs and anal swabs, urine, sputum, saliva, semen, lymphatic fluid, liquor, amniotic fluid, cerebrospinal fluid, peritoneal effusions, feces, pleural effusions, fluid from cysts, synovial fluid, vitreous humor; aqueous humor, bursa fluid, eye washes, eye aspirates, pulmonary lavage, lung aspirates, tissues, including but not limited to, liver, spleen, kidney, lung, intestine, brain, heart, muscle, pancreas and cell cultures, bacteria, microorganisms, viruses, plants, fungi including samples that derive from the foregoing or comprise the foregoing. Materials obtained from clinical or forensic settings or environmental samples such as soil that contain or are suspected to contain nucleic acids are also within the intended meaning of the term biological sample.

Furthermore, the skilled artisan will appreciate that extracts, or materials or portions thereof obtained from any of the above exemplary samples are also within the scope of the term sample. Preferably, the sample is derived from a human, animal, plant, bacteria or fungi. Preferably, the sample is derived from a human or animal. Preferably, the sample is selected from the group consisting of cells, tissue, bacteria, viruses and body fluids such as for example blood, blood products such as buffy coat, plasma and serum, urine, liquor, sputum, stool, CSF and sperm, epithelial swabs, vaginal swabs, cervix samples, biopsies, bone marrow samples and tissue samples, preferably organ tissue samples such as lung and liver. The sample may be stabilized. Certain samples such as blood samples are usually stabilised upon collection, e.g. by contacting them with a stabilizer such as an anticoagulant in case of blood and samples derived from blood. Also fixed samples such as e.g. FFPE samples can be processed using the teachings described herein.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to all types of DNA and/or RNA, e.g. gDNA; circular DNA; plasmid DNA; circulating DNA; PNA; LNA, cyclohexene nucleic acids; RNA/DNA hybrids; hnRNA; mRNA; non-coding RNA (ncRNA), including but not limited to rRNA, tRNA, miRNA (micro RNA), siRNA (small interfering RNA), snoRNA (small nucleolar RNA), snRNA (small nuclear RNA), pwi-interacting RNA (piRNA), repeat associated RNA (rasiRNA), as RNA and stRNA (small temporal RNA); fragmented nucleic acids; nucleic acid obtained from subcellular organelles such as mitochondria or chloroplasts; and nucleic acid obtained from pathogens, microorganisms, parasites, or DNA or RNA viruses that may be present in a biological sample, e.g. bacteria, viral or fungi nucleic acids; synthetic nucleic acids, extracellular nucleic acids. The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. The term "extracellular nucleic acids" refers e.g. to extracellular RNA as well as to extracellular DNA. Examples of typical extracellular nucleic acids that are found in the cell-free fraction (respectively portion) of biological samples such as body fluids such as e.g. blood plasma include but are not limited to mammalian extracellular nucleic acids such as e.g. extracellular tumor-associated or tumor-derived DNA and/or RNA, other extra-cellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses or fungi.

The lysate that is obtained with the present invention can be used directly in a nucleic acid amplification reaction. As described herein, "directly" in this respect means that it is not necessary to isolate and in particular to purify the nucleic acids comprised in the lysate prior to performing the amplification reaction. Therefore, no nucleic acid isolation or purification is performed prior to performing the amplification reaction. However, as described herein it is within the scope of the present invention to further process the lysate prior to subjecting at least an aliquot thereof to the nucleic acid analysis method. E.g. the lysate may be cleared and at least an aliquot of the cleared lysate is then used in the amplification reaction. Furthermore, the obtained lysate may also be treated with enzymes such as RNases, DNases and/or a reverse transcriptase prior to performing the nucleic acid analysis method.

According to one embodiment, an aliquot of the obtained lysate, which is optionally cleared, can be contacted with reagents that are required for performing an amplification reaction. According to one embodiment, the lysate, which is optionally cleared, is added to an aqueous solution comprising reagents that are necessary for performing an amplification reaction. The amount of used lysate, which is optionally cleared, that is added to the composition comprising the reagents for performing the analysis method such as e.g. the amplification reaction and hence is comprised in the resulting mixture can largely vary and can be chosen e.g. from 1% to 98%, 1% to 95%, 5% to 85%, 10% to 75% and 15% to 70%. Hence, the lysate which is optionally cleared, can be used in small amounts as well as in rather large amounts in the analysis reaction such as the amplification reaction. The teachings of the present invention in particular have a positive effect if high amounts of lysate is added because the sensitivity can be improved.

Furthermore, a lysate that was obtained using the teachings of the present invention can also be used to reconstitute a dry composition, preferably a freeze-dried composition, comprising reagents for performing an amplification reaction. Also in this case, at least a portion of the lysate is used in the amplification reaction in the sense of the present invention. The dry composition comprises one or more reagents necessary for performing the intended amplification reaction. Preferably, the dry composition comprises at least one polymerase. According to one embodiment, the dry composition is a freeze-dried composition. Freeze-dried compositions are widely used for providing reagents necessary for amplification reactions in a storable form. Methods for preparing respective freeze-dried compositions as well as suitable additives that stabilise the comprised reaction compositions, in particular biochemical components such as proteins are well-known in the prior art (see e.g. Freeze-Drying/Lyophilization of Pharmaceutical and Biological Products, Second Edition, WO 01/92569, WO 2010/001162, US 2010/0068716 and US 2010/0159529) and thus, need no detailed description here. The dry composition that can be used in the method according to the present invention is a storable composition. Preferably, it is suitable for long-term storage. According to one embodiment, the dry composition is stable during storage for a time period of at least 3 months, at least 6 months, at least 10 months or at least 12 months. Preferably, the dry composition is stable for a time period of 3 to 18 months or 6 to 12 months. According to one embodiment, the dry composition comprises at least some of the chemical and/or biochemical reagents necessary for conducting the intended analysis method. Preferably, it comprises all of the necessary amplification reagents because upon addition of the lysate the composition is ready for performing the analytical method. This is particularly advantageous when using the method e.g. in a LoC system. According to a preferred embodiment, the dry composition comprises at least some, preferably all, of the reagents necessary for conducting the amplification reaction, preferably a PCR reaction. As discussed above, respective dry compositions, in particular freeze-dried compositions, are widely used to provide the reagents necessary for an amplification reaction in form of a so-called master mix, in a storable form. When intending to perform the amplification reaction, the dry composition only needs to be reconstituted using the lysed sample to form the amplification reaction mixture, wherein, however, optionally further reagents can be added e.g. if not all reagents were already comprised in the dry composition, what is, however, preferred. Preferably, the dry composition comprises one or more, preferably all reagents selected from the group consisting of a polymerase, a reaction buffer suitable for performing an amplification reaction and dNTPs. Preferably, it also comprises primers and/or labelled probes which allow e.g. the detection the presence or absence of one or more target nucleic acids that are, e.g., indicative of a certain disease or infection. However, they may also be added separately. After reconstitution using the lysate and optionally the addition of further additives, such as primers and/or probes, the resulting reconstituted composition is ready for performing the amplification of a target nucleic acid. According to one embodiment, at least 60%, at least 70%, at least 80%, at least 90%, at least 95% or 100% of the liquid that is used for reconstitution is provided by the lysate. Reconstitution can be advantageously achieved exclusively by addition of the lysate. According to one embodiment, at least an aliquot of the lysate, which optionally is further processed such as cleared in advance, that was obtained as described above, is contacted with the dry composition for reconstitution. In order to ensure that the reconstituted composition comprises the reagents in a concentration appropriate for the intended analysis method, a predetermined amount of lysate is added to the dry composition. Said predetermined amount is chosen such so that in the reconstituted composition, the reagents are comprised therein in a concentration suitable for performing the amplification reaction. The reconstitution process can be assisted by agitation e.g. by pipetting the resulting mixture up and down, stirring, shaking or vortexing. Thereby, an inexpensive, simply manageable complete nucleic acid analysis process is provided which has a high safety standard due to the integrated control that is provided by the method according to the present invention. The method can be advantageously used in conjunction with portable analysis systems capable of performing nucleic acid testing quickly and conveniently on 'integrated' miniaturized devices, also referred to "Lab-on-a-Chip" (LoC) systems.

The amplification reaction can be performed in order to amplify, identify, detect and/or quantify a target nucleic acid contained in or suspected to be contained in a biological sample. Preferably, the amplification reaction allows to detect the presence, absence and/or quantity of nucleic acids comprised in the lysate. Preferably, said method comprises the amplification of at least one target nucleic acid and the subsequent detection of the generated amplicon using e.g. labelled probes. Respective methods are well-known in the prior art and are also commonly applied in the medical, diagnostic and/or prognostic field in order to analyse nucleic acids or a specific target nucleic acid in a biological sample. Hence the amplification method may comprise an analysis of nucleic acids comprised in the lysate to identify the presence, absence and/or severity of a disease state including but not being limited to a multitude of neoplastic diseases, in particular premalignancies and malignancies such as different forms of cancers. E.g. the lysate can be analysed in order to detect diagnostic and/or prognostic markers (e.g., tumor-derived nucleic acids) and/or pathogen nucleic acids. The present invention is suitable in many fields of application, including but not limited to disease screening, oncology, cancer screening, early stage cancer screening, premalignancy screening, cancer therapy monitoring, genetic testing (genotyping), infectious disease testing, testing for pathogens, injury diagnostics, trauma diagnostics, transplantation medicine or many other diseases and, hence, are of diagnostic and/or prognostic relevance.

Basically any nucleic acid amplification method can be performed on the obtained lysate including, but not limited to, polymerase chain reaction (PCR), e.g. reverse transcription polymerase chain reaction (RT-PCR), quantitative real time polymerase chain reaction (qPCR), asymmetric PCR, allele specific PCR, inverse PCR, LATE (linear after the exponential) PCR, intersequence-specific PCR (ISSR), multiplex PCR, nested PCR, solid support PCR, ligation mediated PCR or methylation-specific PCR (MSP), DNA or RNA sequencing, next generation sequencing, isothermal amplification methods e.g. LAMP (loop mediated isothermal amplification), RPA (recombinase polymerase amplification), HDA (helicase dependent amplification), NEAR (nicking enzyme amplification reaction), TMA (transcription mediated amplification) or NASBA (nucleic acid sequence based amplification), polymerase cycling assembly (PCA), or any combination of the foregoing. Respective technologies are well-known to the skilled person and thus, do not need further description here.

Furthermore, as is also apparent from the amplifications to be performed, it is within the scope of the present invention to further process the lysate prior to subjecting the lysate to the amplification. E. g. a reverse transcription can be performed for obtaining cDNA. Reverse transcription can be performed directly using the obtained lysate. Furthermore, depending on the target nucleic acid to be detected, a DNase or RNase digest can be performed. Respectively processed lysates are also encompassed by the term "lysate" and can be subjected to the amplification reaction.

According to one embodiment, the method according to the present invention includes an amplification control. Said amplification control provides an amplification signal if the biological sample was added for obtaining the lysate.

According to one embodiment, the internal amplification control is comprised in the amplification reaction. Here, internal controls that are commonly used in the prior art may be used. Examples were described in the background of the present invention. Incorporating a respective internal control has the advantage that it can be analyzed whether the amplification reaction worked properly. For example, the internal control may be a nucleic acid such as DNA or RNA. If the target nucleic acid to be amplified is RNA, the control preferably also is provided by RNA. The amplification reaction then comprises suitable primers and/or probes that allow to detect the internal control under the used amplification conditions. If sufficient biological sample was added for obtaining the lysate and the amplification worked properly, the internal control will give a positive signal in the amplification reaction. If no amplification signal is achieved for the internal control, this indicates that the diagnostic assay did not work properly. Thereby also amplification reactions can be identified as invalid wherein no sufficient biological sample material was added because in this case, the presence of compound (A) in the lysate also inhibits the amplification of the internal control. Therefore, incorporating a respective internal control has advantages when being used in combination with the control principle according to the present invention.

According to one embodiment, the amplification control is performed in a parallel amplification reaction, wherein said amplification reaction comprising the amplification control is prepared using the same lysate that is used in the amplification reaction. Thereby it is ensured that compound (A) can inhibit the amplification of the control if no or not enough sample material was used for preparing the lysate.

According to one embodiment, the amplification control is provided by a nucleic acid that is added separately from the lysate to the amplification reaction. However, the amplification control may also be comprised in the lysate. E.g. house-keeping genes could be detected as amplification control.

The amplification result that is obtained for the amplification control can be used to determine and/or indicate whether the amplification result and thus the performed test or assay is valid. The amplification control provides an amplification signal only if sufficient biological sample material was added for obtaining the lysate and wherein an amplification reaction, wherein no amplification signal is obtained for the internal amplification control indicates and preferably is reported as invalid test result. Some examples will be illustrated subsequently. If the amplification control and the target nucleic acid are detected in the same amplification reaction, i.e. in the same reaction vessel, said amplification reaction comprises all primers and/or probes that are necessary to detect the target nucleic acid (Amp-1) and the internal control (Amp-2). Alternatively, as described above, two separate amplification reactions are performed in parallel, however, using the same lysate. In both alternatives it is possible to either separately add the template for the amplification control. However, said template for Amp-2 may also be provided by the lysate that is subjected to the amplification reaction. The following amplification results could be obtained:

1) Amp-1=pos. and Amp-2=pos. or Amp-1=pos. and Amp-2=neg. (positive means that an amplicon is detected). This result indicates that the test is valid and that the target nucleic acid was detected.

2) Amp-1=neg. and Amp-2=pos. This result indicates that the test is valid and that the target nucleic acid was not detected.

3) Amp-1=neg. and Amp-2=neg. This result indicates that the test is invalid and must be repeated.

According to a second aspect, a method is provided for amplifying a nucleic acid comprising subjecting a lysate to an amplification reaction, wherein said amplification reaction comprises at least one compound (A) which comprises at least one anionic group, wherein compound (A) inhibits the amplification reaction if no sufficient biological sample material was added for obtaining the lysate but does not inhibit the amplification reaction if sufficient biological sample material was added for obtaining the lysate and wherein said method comprises analyzing the amplification result, wherein due to the presence of compound (A) in the amplification reaction, no amplification signal is obtained if no sufficient biological sample material was added for obtaining the lysate but wherein an amplification signal is obtained if sufficient biological sample material was added for obtaining the lysate.

Details regarding suitable and preferred embodiments of compound (A), suitable and preferred concentrations of compound (A), suitable and preferred embodiments for obtaining the lysate and suitable and preferred embodiments for the amplification reaction, the use of amplification controls and the like were described above in conjunction with the method according to the first aspect. It is referred to the above disclosure which also applies here.

Numeric ranges described herein are inclusive of the numbers defining the range. The headings provided herein are not limitations of the various aspects or embodiments of this invention which can be read by reference to the specification as a whole. The term "solution" as used herein, in particular refers to a liquid composition, preferably an aqueous composition. It may be a homogenous mixture of only one phase but it is also within the scope of the present invention that a solution that is used according to the present invention comprises solid components such as e.g. precipitates. The term "carboxylate" as used herein also refers to protonated carboxylate groups, e.g. carboxyl groups, since depending on the pH value always a certain amount of the carboxylate groups is protonated. Thus, as used herein, the terms "carboxylate" "carboxyl group" are used interchangeably and shall refer to the carboxyl group (COOH), the carboxylate anion (COO$^-$) or the carboxylate salt [—COO$^{(-)}$X$^{(+)}$]. Likewise, the term "acid" as used herein also refers to the salts of the respective acid, i.e. to the deprotonated form of the acid and vice versa. Thus, contacting the sample with at least one water-soluble polyanionic polymer during lysis e.g. also comprises adding a respective polymer with anionizable groups which becomes a polyanionic polymer under the conditions used during lysis and thus e.g. in the lysis mixture.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

This invention is not limited by the exemplary methods and materials disclosed herein. The invention will now be described by the following, non-limiting examples.

EXAMPLES

Example 1

Blood was used as sample material. The lysis buffer comprised: 0.1% PVP (MW 10.000), 0.45% Tween-20, 0.45% Nonidet P40, 70 mM Tris/HCl pH 8.0, 1 mM EDTA, 0.04% PAA, 0.025% proteinase K-solution, 65 µl carboxylated magnetic particles per ml lysis buffer, 50 mg Amberlite XAD-7 per ml lysis buffer, 20 µl chelex-suspension per ml lysis buffer. This lysis buffer comprises PAA as compound (A). PAA is capable of depleting inhibitors released from the biological sample, thereby improving the subsequent amplification reaction. However, PAA itself is a PCR inhibitor. Thus, if no biological sample material is added during lysis, PAA inhibits the amplification. PVP, the carboxylated particles, Amberlite XAD-7 and Chelex are additives that were used in addition to PAA in order to further deplete inhibitors that are released from the complex sample blood during lysis. The used non-ionic detergents assist the lysis of the sample. The respective lysis buffer was contacted with 10 volume % whole blood and 1 ng genomic DNA of N. gonorrhoeae. The genomic DNA of N. gonorrhoeae served as target nucleic acid that was supposed to be detected in the amplification reaction. Respective pathogen nucleic acids are commonly detected in diagnostic assays using whole blood. The references comprised the same amount of lysis buffer and the same amount of genomic DNA, however, did not comprise blood. I.e. in the references, no biological sample material was added during lysis. The lysate was obtained by heating the lysis mixture for 5 minutes at 95° C. and cooling at room temperature. The carboxylated magnetic beads were magnetically separated. The supernatant of the lysate was added to freeze-dried PCR master mixes.

Thus, exclusively the obtained lysate was used for reconstituting the freeze-dried master-mixes. The reconstituted reaction mixtures were used for performing a quantitative PCR (3 min 95° C. and 40×{5 sec 95° C., 30 sec 60° C.}).

FIG. 1 shows that the amplification reactions that were performed with the lysates that were obtained using blood during lysis showed a typical quantitative PCR signal. However, the reference samples, wherein the lysate was obtained without the addition of blood showed a flat and thus negative amplification signal. Thus, example 1 shows that the method according to the present invention allows to control that a biological sample was added during lysis as an amplification signal is only obtained for these correctly processed lysates. If no biological sample material (here: blood) is added the presence of PAA in the lysate inhibits the amplification reaction.

Example 2

In this example, the following lysis buffers were used:
Buffer 1: 0.1% SB3-14, 10 mM Tris pH8.1, 1 mM EDTA
Buffer 2: 0.1% SB3-14, 10 mM Tris pH8.1, 1 mM EDTA, 0.025 volume % proteinase K
Buffer 3 (reference): FCPL (Fast Lane Kit, QIAGEN). Buffer FCPL renders an amplification compatible lysate (no isolation of the nucleic acids required), however, does not comprise a compound (A).

Nasopharyngeal swabs were used as sample material. One nasopharyngeal swab was swirled in 300 µl of each lysis buffer. 100 µl aliquots were obtained and processed as follows:
  Contacting 100 µl swab sample contained in the lysis buffer or, as reference, the lysis buffer without swab sample with 10 µM SeraMag beads (seradyne; 50 mg/ml-carboxylated beads) and 1 µl MutaGrip vaccine (2007/2008; Roche, which comprises inactivated viruses including their nucleic acids)
  Incubation for 5 minutes at 95° C. at 1400 rpm in a thermo mixer
  Short centrifugation to collect condensate from the lid
  Cooling down for 5 minutes at room temperature
  Magnetic separation of the carboxylated beads (1 minute)
  Collection of the supernatant, which corresponds to the cleared lysate
  Reconstitution of a RT-PCR lyophilisate for detection of influenza B which includes reverse transcriptase (for a 15 µl reaction volume) with 14 µl cleared lysate
  Addition of 1 µl primer/probe mix
  Reaction conditions: 50° C., 10 minutes, 95° C., 5 minutes, 40×{95° C. 5 sec, 60° C. 30 sec, 72° C. 10 sec}.

Figure 2:
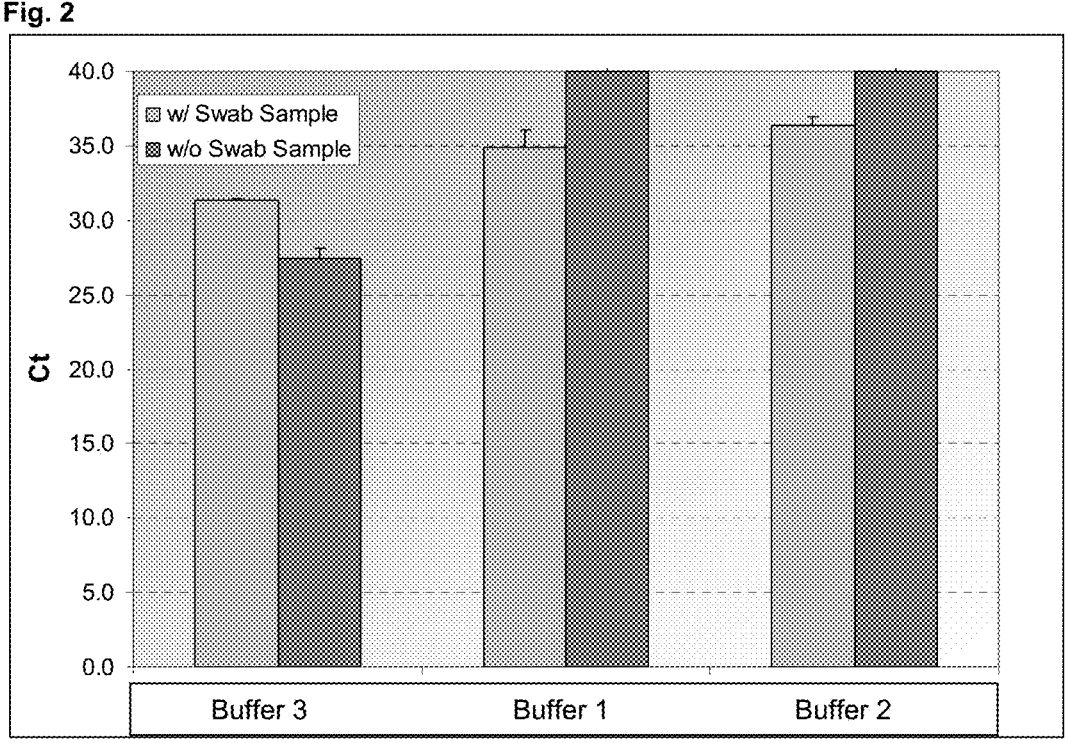
FIG. 2: PCR amplification results showing that no amplification signal is achieved—despite the presence of target nucleic acid—if no biological sample was added during lysis (see example 2).

FIG. 2 shows that the reverse transcription quantitative PCRs from the lysates that were obtained with or without the addition of the sample in order to detect influenza B (shown is the median obtained from duplicates). Reactions, wherein after 40 cycles no amplification was detectable, are shown with a Ct of 40. As can be seen, the lysis buffers comprising a compound (A) according to the present invention (here SB3-14) only obtained an amplification signal if the biological sample was added. If no sample was added, no amplification signal was obtained. An amplification compatible lysis buffer that did not comprise a compound (A) as taught by the present invention (FCPL) obtained a signal irrespective of whether the sample was added or not. Example 2 confirms the advantages of the present invention, as false negatives that might occur due to the fact that no sample was added during lysis can be identified with the control method according to the present invention.

The invention claimed is:

1. A method for determining whether a lysate contains sufficient biological sample material for a nucleic acid amplification reaction, the method comprising:
   a) combining the lysate with a composition, wherein said composition comprises at least one compound (A) selected from the group consisting of a polyacrylic acid and sulfobetaine 3-14, wherein compound (A) inhibits the nucleic acid amplification reaction if no sufficient biological sample material was present during preparation of the lysate but does not inhibit the nucleic acid amplification reaction if sufficient biological sample material was present during preparation of the lysate;
   b) optionally further processing the lysate;
   c) subjecting at least a portion of the lysate to the nucleic acid amplification reaction; and
   d) analyzing a result of the nucleic acid amplification reaction, wherein due to the presence of compound (A) in the nucleic acid amplification reaction, no amplification signal is obtained if no sufficient biological sample material was present during preparation of the lysate but wherein an amplification signal is obtained if sufficient biological sample material was present during preparation of the lysate.

2. The method according to claim 1, wherein if sufficient biological sample material was present during preparation of the lysate, compound (A) prevents or reduces inhibition of the nucleic acid amplification reaction by depleting inhibitors released during lysis of the biological sample material, but wherein compound (A) inhibits the nucleic acid amplification reaction if no sufficient sample material was present during preparation of the lysate and thus no or no sufficient amount of inhibitors were released during lysis.

3. The method according to claim 1, wherein compound (A) is present as a component of a lysis composition that is used for lysing the biological sample during preparation of the lysate.

4. The method according to claim 1, wherein the method includes one or both of the following characteristics:
   i) the lysate is used for reconstituting a dry reagent composition comprising amplification reagents thereby providing an aqueous amplification composition; and
   ii) in step b) the lysate is cleared and a portion of the cleared lysate is subjected in step c) to the nucleic acid amplification reaction.

5. The method according to claim 1, wherein the presence or absence of a target nucleic acid in the biological sample is detected.

6. The method according to claim 1, wherein the method further comprises an amplification control.

7. The method according to claim 6, wherein the method includes one or more of the following characteristics:
   i) the amplification control is an internal amplification control comprised in the nucleic acid amplification reaction;
   ii) the amplification control is performed in a parallel amplification reaction, wherein said parallel amplification reaction comprising the amplification control is prepared using the same lysate that is used in the nucleic acid amplification reaction;
   iii) the amplification control is provided by a nucleic acid that is added separately from the lysate to the nucleic acid amplification reaction;
   iv) the amplification control is present as part of the lysate;

v) the amplification result obtained for the amplification control is used to determine and/or indicate whether the nucleic acid amplification result is valid; and vi) the amplification control provides an amplification signal if sufficient biological sample material was present during preparation of the lysate and wherein an amplification reaction wherein no amplification signal is obtained for the internal amplification control indicates an invalid test result.

8. A method for amplifying a nucleic acid comprising subjecting a lysate to an amplification reaction, wherein said amplification reaction comprises at least one compound (A) selected from the group consisting of a polyacrylic acid and sulfobetaine 3-14, wherein compound (A) inhibits the amplification reaction if no sufficient biological sample material was present during preparation of the lysate but does not inhibit the amplification reaction if sufficient biological sample material was present during preparation of the lysate and wherein said method comprises analyzing a result of the amplification reaction, wherein due to the presence of compound (A) in the amplification reaction, no amplification signal is obtained if no sufficient biological sample material was present during preparation of the lysate but wherein an amplification signal is obtained if sufficient biological sample material was present during preparation of the lysate.

9. The method according to claim 8, wherein the method includes one or both of the following characteristics:

i) the lysate is used for reconstituting a dry reagent composition comprising amplification reagents thereby providing an aqueous amplification composition; and ii) the lysate is cleared and a portion of the cleared lysate is subjected to the nucleic acid amplification reaction.

10. The method according to claim 8, wherein the method further comprises an amplification control, and wherein the method includes one or more of the following characteristics:

i) the amplification control is an internal amplification control comprised in the nucleic acid amplification reaction;

ii) the amplification control is performed in a parallel amplification reaction, wherein said parallel amplification reaction comprising the amplification control is prepared using the same lysate that is used in the nucleic acid amplification reaction;

iii) the amplification control is provided by a nucleic acid that is added separately from the lysate to the nucleic acid amplification reaction;

iv) the amplification control is present as part of the lysate;

v) the amplification result obtained for the amplification control is used to determine and/or indicate whether the nucleic acid amplification result is valid; and vi) the amplification control provides an amplification signal if sufficient biological sample material was present during preparation of the lysate and wherein an amplification reaction wherein no amplification signal is obtained for the internal amplification control indicates an invalid test result.

\* \* \* \* \*